United States Patent
Litsch et al.

(10) Patent No.: US 12,367,604 B2
(45) Date of Patent: Jul. 22, 2025

(54) METHOD AND SYSTEM FOR OPTICALLY DETECTING THE POSE OF AT LEAST ONE INSTRUMENT IN AN OPERATING THEATER

(71) Applicant: Carl Zeiss Meditec AG, Jena (DE)

(72) Inventors: Dominik Litsch, Schorndorf (DE); Stefan Saur, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 356 days.

(21) Appl. No.: 17/856,957

(22) Filed: Jul. 2, 2022

(65) Prior Publication Data

US 2023/0005174 A1    Jan. 5, 2023

(30) Foreign Application Priority Data

Jul. 2, 2021    (DE) .................. 10 2021 206 971.1

(51) Int. Cl.
*G06T 7/70* (2017.01)
*A61B 90/20* (2016.01)
*G01B 11/00* (2006.01)

(52) U.S. Cl.
CPC .............. *G06T 7/70* (2017.01); *A61B 90/20* (2016.02); *G01B 11/002* (2013.01); *G06T 2207/10056* (2013.01); *G06T 2207/20081* (2013.01); *G06T 2207/30204* (2013.01); *G06T 2207/30244* (2013.01)

(58) Field of Classification Search
CPC ............. G06T 7/70; G06T 2207/10056; G06T 2207/20081; G06T 2207/30204; G06T 2207/30244; A61B 90/20; G01B 11/002
See application file for complete search history.

(56) References Cited

U.S. PATENT DOCUMENTS

| | | | |
|---|---|---|---|
| 7,742,176 B2 | 6/2010 | Braunecker et al. | |
| 9,392,931 B2* | 7/2016 | Urban | A61B 1/00149 |
| 9,494,518 B2* | 11/2016 | Yang | G01N 21/6458 |
| 10,045,831 B2* | 8/2018 | El-Haddad | H04N 13/239 |
| 10,191,268 B2* | 1/2019 | Leger | G02B 21/16 |

(Continued)

FOREIGN PATENT DOCUMENTS

EP    1664674 B1    4/2013

OTHER PUBLICATIONS

Sarmadi, Hamid et al. "Simultaneous Multi-View Camera Pose Estimation and Object Tracking With Squared Planar Markers", IEEE Access 7 (2019): 22927-22940, Jan. 31, 2019.

(Continued)

*Primary Examiner* — Anand P Bhatnagar
(74) *Attorney, Agent, or Firm* — Ewers IP Law PLLC; Falk Ewers

(57) ABSTRACT

A system and a method for optically detecting a pose of at least one instrument in an operating theater are provided. The method includes determining pose information of the at least one instrument with an optical pose detection device of a surgical microscope or with a microscope-external optical pose detection device, determining whether the pose information is biunique or whether a biunique determination of the pose of the instrument is possible, and evaluating additional information for determining additional pose information, at least for a case where no biunique determination of the pose is possible.

15 Claims, 4 Drawing Sheets

(56) References Cited

U.S. PATENT DOCUMENTS

| | | | |
|---|---|---|---|
| 10,786,323 B2* | 9/2020 | Ang | A61B 90/98 |
| 11,062,465 B2* | 7/2021 | Stopp | G06T 7/70 |
| 2003/0031349 A1* | 2/2003 | Giorgi | A61B 90/20 |
| | | | 382/128 |
| 2008/0208041 A1 | 8/2008 | Gilboa | |
| 2009/0113986 A1* | 5/2009 | Goldbach | A61B 90/06 |
| | | | 73/1.79 |
| 2012/0320186 A1* | 12/2012 | Urban | A61B 34/30 |
| | | | 359/368 |
| 2013/0184571 A1* | 7/2013 | Wilkening | A61B 90/39 |
| | | | 600/426 |
| 2015/0085072 A1 | 3/2015 | Yan et al. | |
| 2016/0324593 A1* | 11/2016 | El-Haddad | A61B 3/13 |
| 2017/0258531 A1 | 9/2017 | Bodjanski | |
| 2019/0228859 A1 | 7/2019 | Moctezuma De La Barrera | |
| 2020/0100847 A1* | 4/2020 | Siegler | A61B 34/20 |
| 2020/0193622 A1* | 6/2020 | Stopp | A61B 90/39 |
| 2021/0186627 A1* | 6/2021 | Winne | A61B 17/00234 |
| 2023/0363830 A1* | 11/2023 | Polchin | A61B 90/20 |
| 2023/0390021 A1* | 12/2023 | Polchin | A61B 90/25 |
| 2024/0299100 A1* | 9/2024 | Minne | A61B 90/20 |

OTHER PUBLICATIONS

Office Action issued in German Patent Application No. DE 10 2021 206 971.1, dated Mar. 7, 2022 (from which this application claims priority) and English language translation thereof.

* cited by examiner

METHOD AND SYSTEM FOR OPTICALLY DETECTING THE POSE OF AT LEAST ONE INSTRUMENT IN AN OPERATING THEATER

CROSS REFERENCE TO RELATED APPLICATIONS

This application claims priority to German patent application DE 10 2021 206 971.1, filed Jul. 2, 2021, the entire content of which is incorporated herein by reference.

TECHNICAL FIELD

The disclosure relates to a method and a system for optically detecting the pose of at least one instrument in an operating theater.

BACKGROUND

The problem of ambiguity when tracking markers and targets is known in the field of detecting poses. This problem arises if output signals of a pose detection device do not allow biunique determination of a pose, that is to say a position and/or orientation, of a marker or a target, with two poses or even more than two poses of this marker/target being able to be assigned to the output signals instead. These ambiguities reduce an accuracy of the pose detection or require complex measures for resolving the ambiguities.

This may especially be the case if, for reasons of space, the number of markers required for the biunique pose determination are not always fastened to objects, more particularly instruments, whose pose is to be determined or the markers are not arranged relative to one another in such a way that such a biunique pose determination is rendered possible. Alternatively or cumulatively, it is possible that, for reasons of space, the number of image capturing devices present is insufficient to facilitate a biunique pose detection.

The related art describes various approaches for resolving such ambiguities. By way of example, the document "Sarmadi, Hamid et al. "Simultaneous Multi-View Camera Pose Estimation and Object Tracking With Squared Planar Markers", IEEE Access 7 (2019): 22927-22940" describes a tracking device consisting of a plurality of cameras, the image representations of a video sequence produced by a plurality of cameras being evaluated and ambiguities also being resolved in the process.

US 2020/100847 A1 describes a support structure for a tracking target, the former disclosing an additional marking with asymmetric properties such that an ambiguity in the position determination can be resolved.

US 2008/208041 A1 describes a system for unique determination of the position of a surgical instrument relative to a body with two cameras and markers, the cameras being part of the surgical instrument. Furthermore, an additional marking has been described, the latter serving to determine the orientation of reference points.

US 2019/228859 A1 describes a machine-vision system for assisting surgical methods, the system including a plurality of devices for determining positions of surgical instruments. Furthermore, the machine-vision system comprises one or more camera(s), with pattern recognition and software being used to detect the position of a surgical instrument. However, resolving ambiguity by using the information from a plurality of devices has not been disclosed.

US 2015/085072 A1 describes a method for resolving ambiguities when using two cameras, with what are known as ambiguous markers being removed.

EP 1 664 674 B 1 describes a method for determining the pose of a hand-held measuring device in space. Said document further explains that one of two possible positions can be excluded for plausibility reasons, for example because it is located underground. The exclusion on account of simple further information, for example the distinction between north and south which can be made using a magnetic compass, is also described.

SUMMARY

A technical problem arising is that of developing a method and a system for optically detecting the pose of at least one instrument in an operating theater, which easily improve an accuracy of the pose detection.

The technical problem is resolved by a method and a system for optically detecting the pose of at least one instrument in an operating theater as described herein.

With regard to the method for optically detecting the pose of at least one instrument in an operating theater, the operating theater can denote a room or room-like region that is set up to carry out operations. In particular, the devices or equipment required to carry out an operation are arranged in the operating theater, these include an operating table, lighting devices, at least one infusion apparatus and devices for anesthetization. In particular, a surgical microscope and a microscope-external pose detection device, or at least parts thereof, are also arranged in the operating theater. However, this list is not exhaustive. The instrument can in particular be a medical instrument, more particularly a surgical instrument. For example, this includes instruments such as clamps, holders, syringes, tweezers, spatulas, scissors, scalpels, wound hooks, forceps, aspirators, cauterizing tools, but also retractors, e.g. a brain retractor. The instrument can in particular be an instrument that can be guided by a user's hand.

Within the meaning of this disclosure, a microscope can designate a device for magnified visual presentation of an examination object. The microscope can be a conventional light microscope, which generates an enlarged image by utilizing optical effects, in particular with beam guidance and/or beam shaping and/or beam deflection, for example lens elements. However, the microscope can also be a digital microscope, wherein the image to be visualized by the microscope can be produced with an image capture device and can be displayed on an appropriate display device, for example a display unit.

The microscope may include a stand for mounting the microscope. The microscope, in particular an objective of the microscope, may be mechanically fastened to a free end of the stand, in particular movably, e.g., pivotably. The stand is in this case configured in such a way that it permits a movement of the microscope in space, in particular with at least one degree of freedom, typically with six degrees of freedom.

It is of course also possible that the stand is configured such that it permits movement of the microscope in space with a restricted number of degrees of freedom, that is to say in particular with fewer than six degrees of freedom. Moreover, the stand can include at least one drive device for moving the microscope. The stand typically includes multiple drive devices.

In particular, it is possible for the at least one drive device to be actuated such that the microscope, in particular the objective, executes a desired movement and thus a desired change of pose in space or adopts a desired pose in space. Such a microscope can also be referred to as a robotic microscope.

For example, the at least one drive device can be actuated such that an optical axis of the objective adopts a desired orientation. Moreover, the at least one drive device can be actuated such that a reference point of the microscope, e.g., a focal point, is positioned at a desired position in space.

A target pose in this instance can be specified by a user or by another superordinate system. Methods for controlling the at least one drive device on the basis of a target pose and a kinematic structure of the stand are known here to the person skilled in the art. The user in this instance can refer to a person who operates the microscope, in particular who looks into/through the eyepiece in order to obtain a magnified view of an object. It is possible that the microscope is what is known as a surgical microscope. In this case, the user can be a surgeon, in particular.

The method includes:
determining pose information of the instrument with an optical pose detection device of a surgical microscope or with a microscope-external optical pose detection device,
checking whether the pose information is biunique or facilitates a biunique determination of the pose of the instrument, and
evaluating additional information for determining more accurate pose information, at least for the case where no biunique determination of the pose is possible.

In this case, the pose information can be determined in a reference coordinate system. The reference coordinate system can be a coordinate system that is stationary with respect to the microscope, a coordinate system that is stationary with respect to the microscope-external optical pose detection device, or a coordinate system that differs therefrom, for example a coordinate system that is stationary with respect to the operating theater. The pose information can be determined as pose or as part of the pose of the instrument, with the pose denoting a position and orientation. The pose denotes a position and orientation.

By way of example, a pose of the instrument can be completely defined, more particularly biuniquely defined, by three position values along the axes of the reference coordinate system and by three orientation values, which may be given by angles about these axes. In particular, a position value can be the value of a coordinate along one of the axes of the reference coordinate system.

The orientation values can represent or encode an angle offset between coordinate axes of a coordinate system, which is stationary with respect to the instrument or specific to the instrument and which can likewise be a Cartesian coordinate system, and the coordinate axes of the reference coordinate system in relation to the corresponding axes. Consequently, an instrument-specific coordinate system can be assigned to each instrument. To completely describe the pose of the instrument it is necessary, in particular, to specify/determine three position values and three orientation values.

A non-biunique definition of the pose may be given if the pose information does not facilitate the unique determination of all position and orientation values. Consequently, a biunique determination can also be referred to as a complete determination of the pose.

By way of example, a vertical axis of the reference coordinate system may be oriented parallel and counter to the direction of gravity and/or to a normal of the operating theater floor, the vertical axis being oriented from bottom to top. Directional specifications such as "top", "bottom", "above", "below" may relate to this direction of the vertical axis. A longitudinal axis and a transverse axis can be oriented perpendicular to the vertical axis and perpendicular to one another. These may span a plane which is oriented parallel to the floor or in which the floor is arranged.

The pose can be determined with the assistance of markers. This can mean that exactly one marker or multiple markers is/are arranged on, more particularly fastened to, the instrument. It is also conceivable that a target is arranged on, more particularly fastened to, the instrument, with the target comprising exactly one marker or else multiple markers. If multiple markers are arranged on the instrument or if a target includes multiple markers, these can be arranged relative to one another with a predetermined arrangement, that is to say with an arrangement known in advance. The markers may not in this case be in a collinear arrangement in particular.

A marker can in this case be optically detectable and thus also be detectable in the image representation of an image capturing device of a pose detection device, in particular thus have an optically detectable pattern. An optically detectable marker can in particular be what is known as an ARUCO marker or be a marker embodied as described in US 2017/258531 A1.

A marker is typically a passive marker. A passive marker can in particular be a marker that does not consume any energy in order to be detectable or reliably detectable. Thus, a passive marker also does not have to be supplied with energy, e.g., from an energy storage device such as a battery or from a mains network. This in turn permits a construction with minimal installation space requirements. In particular, a passive marker cannot generate a signal, and in particular cannot emit a signal that is received by a receiving device, in particular by an image capturing device. However, it is also possible that a marker is an active marker. By way of example, the latter can produce a detectable signal, with energy being consumed during the production.

It is further possible that a marker is a reflective or a non-reflective marker, a phosphorescent or non-phosphorescent marker, and/or a fluorescent or non-fluorescent marker.

The pose detection device of the microscope, also referred to as internal pose detection device below, is typically a monoscopic pose detection device. The latter includes at least one image capturing device, in particular exactly one image capturing device, for producing two-dimensional image representations of at least one marker, with a pose, that is to say a three-dimensional position and/or a three-dimensional orientation, of the marker being able to be determined by evaluating a two-dimensional image representation, in particular exactly one two-dimensional image representation. In particular, an evaluation of intensity values of pixels (image points) of the two-dimensional image representation can be carried out in order to determine the pose.

The internal pose detection device, however, need not necessarily be in the form of a monoscopic pose detection device; it may also be configured differently, for example as a stereoscopic pose detection device.

The image capturing device(s) of the internal pose detection device can be arranged in a housing of the microscope in this case. Furthermore, a beam path for radiation used for the microscopic imaging can be arranged and/or formed to be different, in particular spatially separated, from the beam path for radiation guided to the image capturing device of the internal pose detection device and used for determining the pose. The beam paths can be formed in a common housing or microscope body of the microscope. Captured regions of these image capturing devices can overlap at least in part.

The microscope-external optical pose detection device, also referred to as external pose detection device below, may include exactly one image capturing device or at least two image capturing devices. In particular, the external pose detection device may include the image capturing devices of a stereo camera system, but this is not mandatory. Consequently, the external pose detection device can be a stereoscopic pose detection device. The image capturing device(s) of the external pose detection device may be configured to capture infrared radiation. By way of example, a stereo camera system, for example from NDI, can be used as an external pose detection device.

Further, a pose detection device, that is to say the internal and/or the external pose detection device, may include at least one lighting device. The latter can be configured to produce radiation, for example radiation with wavelengths in the wavelength range of infrared radiation, in particular exclusively in the wavelength range of infrared radiation.

In this case, the pose information can be determined with an evaluation device of the pose detection device. This may be formed as a microcontroller or an integrated circuit or include such a microcontroller or integrated circuit. To this end, output signals generated by the image capturing device(s) (image signals) can be transferred to the evaluation device and can be evaluated by the latter for the purposes of determining the pose.

Further, there is a check, in particular by the evaluation device or a further evaluation device, as to whether the pose information is biunique or facilitates a biunique determination of the pose of the instrument, in particular on the basis of the pose information. In the case of biunique pose information there only exists exactly one pose of the instrument in which this pose information is determined by the pose detection device.

In particular, the pose information is precisely not a biunique item of pose information or the pose of the instrument can precisely not be determined biuniquely if the same pose information is determined by the pose detection device in at least two different poses of the instrument. If the check is carried out by a further evaluation device, that is to say by an evaluation device that differs from the evaluation device of the pose detection device, the pose information can be transferred to this evaluation device, in particular by a suitable means for data transfer.

In particular, the check can be carried out within the scope of the image evaluation which is carried out to determine pose information or the pose of the instrument.

Further, evaluating additional information for determining more accurate pose information, at least for the case where no biunique determination of the pose is possible, is in particular likewise carried out by the evaluation device or the further evaluation device. Hence, more accurate pose information is determined. By way of example, a more accurate determination can be facilitated if the evaluation of the additional information—in comparison with the pose information without an evaluation of the additional information—facilitates the determination of a further position value and/or a further orientation value, or reduces or resolves an ambiguity of at least one position value and/or at least one orientation value.

By way of example, the additional information facilitates the determination of a position or part of a position and/or an orientation or part of an orientation of the instrument in the reference coordinate system and/or relative to a device or an object in the operating theater. Part of the position can be a position value along an axis. Part of an orientation can be part of an orientation value relative to/about an axis. Thus, the additional information can be pose information, in particular additional pose information.

The additional information can increase the information content of the pose information determined by the pose detection device, which is also referred to as initial pose information below. Hence, the pose can be determined more accurately on the basis of the combined information, in particular fused information, that is to say the combination/fusion of initial pose information and additional information, than in the case where the pose is determined without considering the additional information. In this case, the combined pose information denotes the totality of initial pose information and additional information. By way of example, ambiguity in the initial pose information can be resolved by the additional evaluation of the additional information.

By way of example, if a position value can only be determined along one axis of the reference coordinate system on the basis of the initial pose information, position values along two or three axes of the reference coordinate system may be determined on the basis of the combined pose information. By way of example, if the position value along an axis and/or the orientation value in relation to an axis of the pose of the instrument is not uniquely determinable on the basis of the initial pose information (for example, because two or more position values and/or two or more orientation values yield the same pose information), this ambiguity can be resolved on the basis of the combined pose information.

Typically, the additional pose information can facilitate a biunique determination of the pose, but this is not mandatory. If a biunique determination is possible, the position values along three axes of the reference coordinate system and the orientation values about these three axes can be determined on the basis of the combined pose information.

By way of example, triangulation methods or other heuristics/rules can be applied for the purposes of determining the pose more accurately. By way of example, in order to resolve ambiguities of the position and/or rotation values, it may be sufficient if regions with the same relative pose to one another along at least one axis and/or about an axis of the reference coordinate system, for example an upper region and a lower region, or regions with the same pose along at least one axis and/or about an axis of the reference coordinate system, can be identified in the reference coordinate system in the image representations for determining the pose and in an image representation of the additional information.

As a result, a detection of the pose of the instrument in the operating theater, which is easily implementable and more accurate, can advantageously be attained. In turn, this can advantageously be used for applications such as pose tracking or an overlay of the pose of the instrument in data records produced presurgery, for example.

In particular, the method advantageously facilitates the use of cameras in the operating theater for the purposes of determining the pose, the actual (primary) task of which cameras is not the determination of the pose but, for example, a visual reproduction of the situs. Consequently, a more accurate determination of the pose is facilitated using components that, as a rule, are already present.

In a further exemplary embodiment, the pose information of the instrument is determined by the microscope-external optical pose detection device and the additional information is produced by evaluating at least one image representation produced by an image capturing device of the surgical microscope. The image capturing device of the surgical microscope can be a constituent part of the aforementioned pose detection device of the surgical microscope, that is to say of the internal pose detection device, with this also being able to be referred to as a surround camera. In particular, this image capturing device can be an image capturing device for the aforementioned monoscopic determination of the pose.

Alternatively, the image capturing device can be an image capturing device for microscopic imaging. The image capturing device for microscopic imaging can produce an image representation of a captured region that is magnified by the microscope optics. In this case, the image capturing device of the internal pose detection device and the image capturing device for microscopic imaging can be image capturing devices that differ from one another. Further alternatively, the additional information can be produced by an image capturing device for producing topographic information, which is arranged on the microscope or is part of the microscope. It is also possible that the additional information is produced by evaluating image representations that were produced by a plurality of mutually different image capturing devices of the surgical microscope.

The captured regions of the microscope-external pose detection device and of the image capturing device of the surgical microscope may overlap in this case. What advantageously arises as a result is that image representations produced by the microscope, which are produced when using the microscope during the operation, even in the context of other applications, for example for a magnified representation, can be used for improving the determination of the pose by a microscope-external pose detection device.

In a further exemplary embodiment, the pose information of the instrument is determined by the optical pose detection device of the surgical microscope, that is to say by the surround camera in particular, and the additional information is produced by evaluating at least one image representation produced by an image capturing device of the surgical microscope which is not a constituent part of the pose detection device. This image capturing device can be the aforementioned image capturing device for microscopic imaging or the likewise aforementioned image capturing device for topographic imaging.

Alternatively, the additional information is produced by evaluating at least one image representation which was produced by exactly one or at least one image capturing device of a microscope-external pose detection device. It is also possible that the additional information is produced by evaluating image representations that were produced by a plurality of mutually different image capturing devices of the microscope-external pose detection device. It is possible that this evaluation differs from an evaluation for determining pose information by the external pose detection device. Expressed differently, the additional information can therefore be no pose information determined by the external pose detection device. It is possible that the additional information is incomplete pose information determined by the external pose detection device.

In particular, this image capturing device can be a constituent part of the aforementioned monoscopic or stereoscopic microscope-external pose detection device. The captured regions of the microscope-external pose detection device and of the image capturing device of the surgical microscope may overlap in this case. Advantageously this results in image representations produced by an external pose detection device being able to be used to improve the determination of the pose by a microscope-internal pose detection device.

In a further exemplary embodiment, a captured region of the image capturing device is increased, in particular maximized, for the purposes of producing the image representation by the image capturing device of the surgical microscope. To this end, at least one optical element of microscope optics which may be a constituent part of the microscope can be moved and/or deformed in particular. Advantageously, this yields a greater information content of this image representation in relation to the additional information. Expressed differently, information content of the additional information, and hence also of the combined pose information, can be advantageously increased as a result of the increased, in particular maximized, captured region.

In a further exemplary embodiment, the more accurate pose information is additionally determined on the basis of information about a relative pose between a coordinate system of the optical pose detection device and an image coordinate system of the image representation evaluated for the purposes of determining the additional information. This relative pose may be known or determined in full or else only in part, that is to say incompletely. By way of example, the relative pose may be known in full if all position values and all orientation values are known in relation to the reference coordinate system. By way of example, the relative pose may be known only in part if not all position values and/or not all orientation values are known in relation to the reference coordinate system.

The relative pose advantageously facilitates the determination of a spatial relationship between the initial pose information and the additional information, as a result of which, in turn, the information content of the combined pose information is increased in relation to the ability to determine a pose of the instrument.

In a further exemplary embodiment, the information about the relative pose is determined at the run-time or is known in advance. It is possible that the information about the relative pose known in advance is determined by way of a calibration or registration method. This advantageously results in a simple and uncomplicated determination of the pose information.

The relative pose can also be determined at run-time. This is illustrated in even more detail below. Advantageously, a more accurate determination of the pose information over the entire run-time emerges as a result thereof.

In a further exemplary embodiment, the information about the relative pose is determined by virtue of the pose of the image capturing device for producing the image representation evaluated for the purposes of determining the additional information being determined by the optical pose detection device, that is to say in particular a pose in a pose detection device-specific coordinate system.

It is possible for at least one marker to be arranged on the image capturing device or stationary relative to the image capturing device, said at least one marker being detected by the optical pose detection device for determining the pose. In particular, it is possible that an external pose detection device determines a pose of the microscope and hence also of an image capturing device of the microscope for the purposes of determining the relative pose.

It is also possible for the information about the relative pose to be determined by virtue of the pose of the optical pose detection device being determined by evaluating the image representation evaluated for the purposes of determining the additional information and produced by an image capturing device, that is to say in particular a pose in an image capturing device-specific coordinate system. Expressed differently, the pose of the optical pose detection device can be determined relative to the image capturing device for producing the image representation in this image representation evaluated for the purposes of determining the additional information. Consequently, this image representation for producing the additional information also serves to determine the relative pose.

It is possible for at least one marker to be arranged on the optical pose detection device, in particular on the external pose detection device or stationary relative to this pose detection device, said marker being detected by the image capturing device for determining the information about the relative pose.

Further alternatively or cumulatively, the information about the relative pose is determined by virtue of a heuristic being applied. In particular, a heuristic can denote an assumption about relative pose information or about pose information in relation to the pose of the coordinate system of the optical pose detection device or in relation to the pose of the image coordinate system of the image representation.

By way of example, a heuristic can consist of the assumption that an external pose detection device may be positioned anywhere in the operating theater but is arranged in such a way that the upper image region of an image representation produced by an image capturing device of this pose detection device images a region of the operating theater which, in relation to the reference coordinate system, is arranged above a region of the operating theater that is imaged in the lower image region of the image representation.

It is also possible for relative pose information to be determined in the case of a robotic microscope by evaluating output signals of sensors for detecting a pose about rotational axes and/or along linear axes of the stand, these output signals rendering it possible to completely or incompletely determine the pose of an image capturing device of the microscope, that is to say, e.g., of the image capturing device for microscopic imaging or the surround camera, in a reference coordinate system. By way of example, this therefore allows the determination of an alignment of the image capturing device relative to the floor of the operating theater.

In a further exemplary embodiment, at least one item of temporal and/or spatial context information is determined, the additional information being determined by evaluating this context information or the additional information being temporal and/or spatial context information.

Temporal context information can be information about a temporal change in instrument-specific information. By way of example, instrument-specific information can be a movement variable of the instrument, that is to say an acceleration, a velocity or a pose. In this case, this movement variable can be determined in the reference coordinate system, but also relative to other devices in the operating theater. Additionally, instrument-specific information can be information about a state of the instrument, in particular about an operating and/or actuating state, or a state-specific spatial embodiment of the instrument. Temporal context information can also be information about an instrument-specific target value, for example about a target movement variable or about a target state.

Spatial context information can be information about a pose of the instrument, in particular relative to any other device in the operating theater. In this case, this can be determined in the reference coordinate system, but also relative to these other devices in the operating theater. Spatial context information can also be information about a target pose.

Examples of temporal and/or spatial context information will still be explained in more detail below.

In this case, context information can be determined with a device for determining the context information. By way of example, this device can evaluate an image representation produced by the pose detection device, the image representation produced for determining the additional information, the initial pose information, and/or the additional information to determine the context information. Additionally, a temporal succession of a plurality of these image representations or information items, that is to say a sequence, can be evaluated for determining the context information. Target values may be specified by a superordinate system.

This advantageously yields an improvement in the accuracy of the pose detection which can be carried out easily.

In a further embodiment, spatial context information is information
 about the relative pose between the instrument and at least one further object in the operating theater,
 about a target pose of the instrument, in particular a target relative pose in relation to a further object in the operating theater,
 about a relative pose between a plurality of markers.

Naturally, the spatial context information may also comprise a plurality but not all, or else all, of the aforementioned items of information.

It is possible for the instrument, the marker, and/or the further object in the operating theater or the respective pose to be detected by the optical pose detection device for the purposes of determining the spatial context information. It is also possible for the instrument, the marker, and/or the further object in the operating theater to be identified in image-based fashion in an image representation produced by the optical pose detection device or in the image representation evaluated for determining the additional information, that is to say by evaluating image data, for the purposes of determining the spatial context information. In the case of a plurality of markers, these can be arranged on the same instrument or else on various instruments or objects in the operating theater.

The aforementioned spatial context information advantageously facilitates a reliable determination of the context information, and hence also a reliable and easily implementable improvement in the accuracy when detecting the pose.

In a further exemplary embodiment, temporal context information is information
 about a movement of the instrument or at least one instrument marker,
 about a relative movement between the instrument and a further object in the operating theater, and
 about a relative movement between various markers.

Naturally, the temporal context information may also include a plurality but not all, or else all, of the aforementioned items of information.

As already explained, it is also possible in this case for the instrument, the marker, and/or the further object in the operating theater or the respective pose to be detected by the optical pose detection device for the purposes of determining the temporal context information.

It is also possible for the instrument, the marker, and/or the further object in the operating theater to be identified in image-based fashion in an image representation produced by the optical pose detection device or in the image representation evaluated for determining the additional information, that is to say by evaluating image data, for the purposes of determining the spatial context information. In the case of a plurality of markers, these can be arranged on the same instrument or else on various instruments or objects in the operating theater.

By way of example, it is possible for two markers to be arranged on an instrument, with a pose of these two markers being determined by the internal and/or the external pose detection device. By way of example, if a first marker is arranged closer to an instrument tip than a further marker, the assumption can be made, especially in the case of a microsurgical operation scenario, that the first marker will move less over a predetermined course of time than the further marker since there generally are very small movements of the instrument tip in microsurgical applications and, on account of the assumed lever effect, the assumption can be made that the further marker tends to perform greater movements. Consequently, the first and the further marker can be identified on the basis of the evaluation of the temporal movement pattern, as can information about an orientation of the instrument which in turn represents additional information about the pose of the instrument. For the aforementioned embodiment, it may further be necessary to determine information, known in advance, about an instrument geometry or an instrument design, in particular about a relative pose of the markers relative to one another on an instrument. This will be explained in more detail below.

The aforementioned temporal context information advantageously facilitates a reliable determination of the context information, and hence also a reliable and easily implementable improvement in the accuracy when detecting the pose.

In a further exemplary embodiment, the at least one item of spatial and/or temporal context information is additionally determined on the basis of information about an instrument geometry and/or instrument design, this being known in advance or determined at run-time.

By way of example, it is possible for an instrument identifier, especially in the form of an ID, to be determined in image-based fashion and for information about the instrument geometry, known in advance, to then be retrieved from a memory device, with information about the instrument geometry and/or instrument design of various instruments being able to be stored in a manner assigned to the corresponding instrument identifiers in said memory device. By way of example, an instrument identifier can be encoded by an instrument-specific configuration of one or more marker(s) and/or by an instrument-specific spatial arrangement of one or more marker(s) relative to one another or relative to an instrument-specific reference point, for example a tip of the instrument. This renders it possible to determine the instrument identifier at run-time.

This facilitates an identification of an instrument in a plurality of produced image representations, for example image representations produced successively in time, and hence also the determination of instrument-specific context information on the basis of these image representations.

Further, it is possible that information about a relative pose between instrument and the image capturing device can be determined on the basis of the instrument geometry, which as explained above is known in advance, and an instrument geometry determined in image-based fashion. Particularly in the case of imaging parameters known in advance, it is possible to determine how the instrument with the geometry known in advance and the image capturing device would have to be arranged relative to one another so that the instrument is imaged in accordance with the instrument geometry determined in image-based fashion. The instrument geometry in the image representation can for example be determined by methods of segmentation or object detection known to a person skilled in the art. This information about the relative pose determined in this way can form the additional information or part of the additional information.

It is also possible that information about a pose of the instrument in the reference coordinate system and/or information about a pose of the instrument relative to a further object in the operating theater can be determined on the basis of the instrument geometry determined in image-based fashion. Thus, for example, an orientation of the instrument, in particular of a longitudinal axis of the instrument, can be determined on the basis of the image-based instrument geometry.

Further, the information about the pose of the instrument in the reference coordinate system and/or relative to a further object can be determined on the basis of this orientation, in particular with a heuristic and/or an instrument identifier being taken into account. By way of example, it is thus possible to assume that an instrument, in particular a predetermined instrument, for example is oriented toward an operating table and/or toward a patient with its tip. This assumption allows the determination of an orientation or part of the orientation and optionally also a position or part of the position of the instrument relative to the operating table and/or patient.

This advantageously yields a simple and reliable determination of context information and hence also a simple and reliable improvement in the accuracy of determining the pose.

In a further exemplary embodiment, the determination of the additional information is a model-based determination and/or the evaluation of additional information for the purposes of more accurately determining the pose information is a model-based evaluation, the model having been produced by machine learning.

Thus, for example, the additional information can be determined using a model, with at least one image representation and/or context information being input variables of the model and the additional information being an output variable of the model.

It is also possible to determine the more accurate pose information using a model, with the initial pose information and the additional information being input variables of the model and the (more accurate) pose information being an output variable.

Additionally, the more accurate pose information can be determined using a model, with the initial pose information and at least one image representation and/or context information being input variables of the model and the (more accurate) pose information being an output variable.

In this case, the term machine learning includes or denotes methods for determining the model on the basis of training data. Thus, it is possible to determine the model using methods for supervised learning, with the training data, that is to say a training data record, to this end including input data and output data.

In this case, data that represent the aforementioned input variables can be provided as input data. In this case, data that represent the aforementioned output variable can be provided as output data.

It is also possible in this case that at least one image representation and/or context information are provided as input data, with the additional information being provided as output data.

In particular, input and output data of such training data can be generated by virtue of these data being produced simultaneously. By way of example, output data can be produced by virtue of the pose of the instrument being determined using a training pose detection device which facilitates a complete and biunique determination of the pose, with this training pose detection device being able to differ from the internal and the external pose detection device.

Input data can then be produced by the internal pose detection device, the external pose detection device, an image capturing device for microscopic imaging and/or a device for determining context information. These data, which in particular are produced simultaneously, then form the input and output data for the training.

For the training there can also be a determination, in particular a complete or biunique determination, of the pose of an instrument having a predetermined number of at least two markers, in particular by way of the training pose detection device. Data representing this biunique pose can then form output data.

Then, some of these data, that is to say a portion of the data that represent the pose information determined by the training pose detection device, can be input data for the training. In particular, the portion of the data cannot facilitate a complete and/or biunique determination of the pose. By way of example, the input data may represent the pose of fewer than the predetermined number of markers. Consequently, a model that facilitates a biunique pose determination from the pose of a few markers can be learnt during the training phase. Then, for example, two markers rather than three or more may be sufficient to biuniquely determine a pose in the inference phase.

Methods for supervised learning are known to a person skilled in the art. It is also conceivable that methods of unsupervised learning are used to determine the model.

Following the creation of the model, that is to say after the training phase, the model, in particular the parameterized model, determined in this way can be used in what is known as the inference phase to then produce the additional information or the (more accurate) pose information from the input data. This yields a reliable and accurate determination of the pose.

It is possible for the model to additionally be determined user-specifically and/or surgery-type-specifically. In this case, user information, in particular a user identifier, and/or surgery type information, that is to say information about the type of surgery carried out, may form a further input variable, both during the training phase and during the inference phase. In this case, the user information and/or the surgery type information can be specified or determined by way of suitable methods. Advantageously, this can further increase an accuracy and reliability of the determination of the pose.

Suitable mathematical algorithms for machine learning include: decision tree-based methods, ensemble methods-based methods (e.g., boosting, random forest), regression-based methods, Bayesian methods-based methods (e.g., Bayesian belief networks), kernel methods-based methods (e.g., support vector machine), instance-based methods (e.g., k-nearest neighbor), association rule learning-based methods, Boltzmann machine-based methods, artificial neural networks-based methods (e.g., perceptron), deep learning-based methods (e.g., convolutional neural networks, stacked autoencoders), dimensionality reduction-based methods, regularization methods-based methods.

In a further exemplary embodiment, the determination of the additional information and/or the evaluation of the additional information is carried out user-specifically or surgery-type-specifically. This has already been explained above.

Further proposed is a system for optically detecting the pose of at least one instrument in an operating theater, the system at least including an optical pose detection device of a surgical microscope or a microscope-external pose detection device and at least one evaluation device, the system being configured to carry out the following steps:

determining pose information of the instrument with the optical pose detection device of a surgical microscope or with the microscope-external optical pose detection device, checking whether a biunique determination of the pose of the instrument is possible on the basis of the pose information, evaluating additional information for determining additional pose information, at least for the case where no biunique determination of the pose is possible.

Consequently the system is configured to carry out a method according to one of the exemplary embodiments described in this disclosure. In this case, the system may also include a plurality of evaluation devices for carrying out the aforementioned steps.

Advantageously, the system facilitates—as explained above—an improvement in accuracy of the pose determination that can be carried out easily.

In a further exemplary embodiment, the system includes at least one image capturing device of the surgical microscope, which is a constituent part of the optical pose detection device of the surgical microscope, and/or at least one image capturing device of the surgical microscope, which is not a constituent part of the optical pose detection device of the surgical microscope. This and corresponding advantages have already been explained above.

BRIEF DESCRIPTION OF THE DRAWINGS

The disclosure will now be described with reference to the drawings wherein.

DESCRIPTION OF EXEMPLARY EMBODIMENTS

Identical reference signs hereinafter denote elements having identical or similar technical features.

Figure 1:
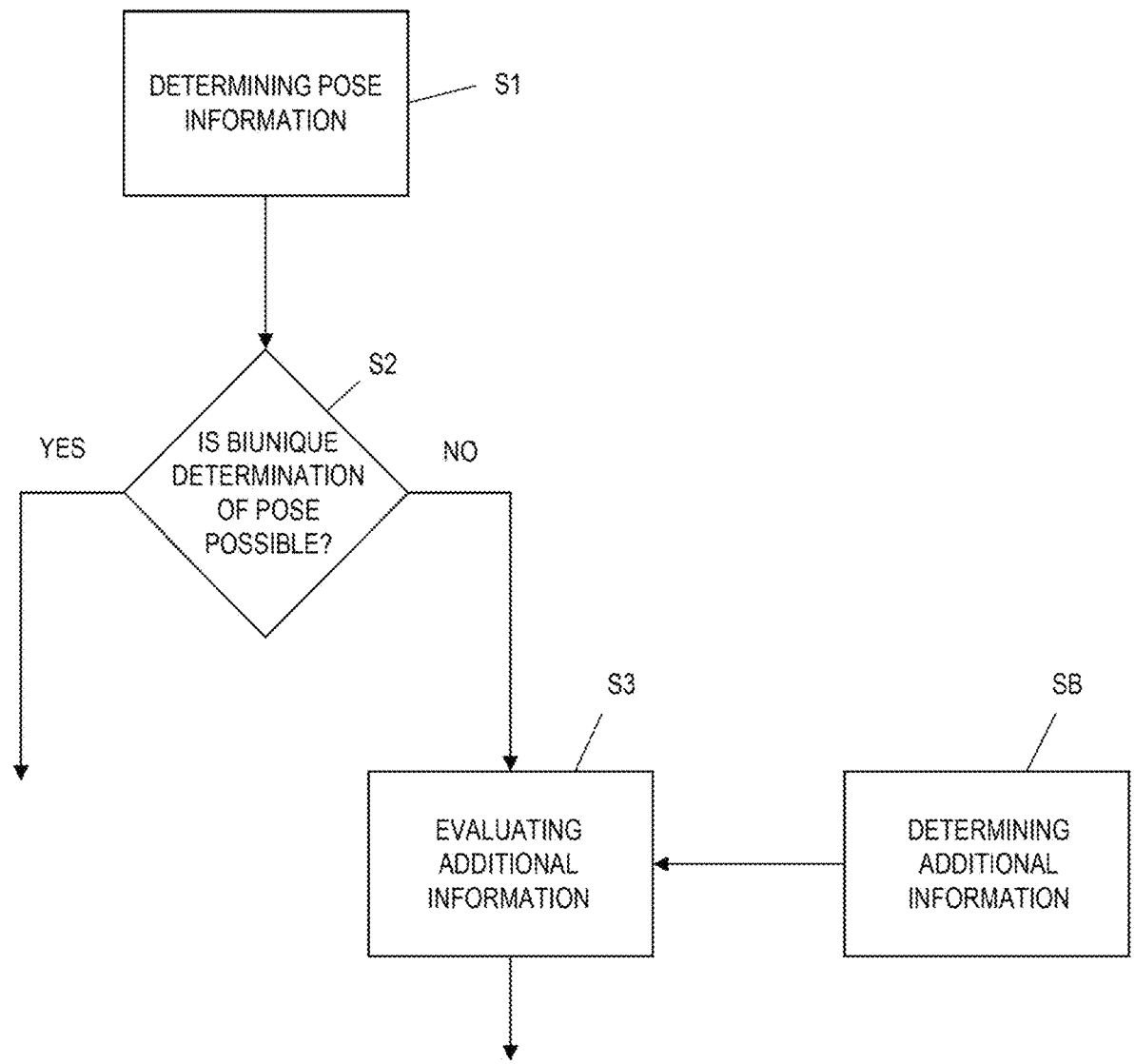
FIG. 1 shows a schematic flowchart of a method according to a first exemplary embodiment of the disclosure.

FIG. 1 shows a schematic flowchart of a method according to a first exemplary embodiment of the disclosure. Pose information regarding an instrument 2 (see FIG. 3) is determined in a first step S1 by an optical pose detection device of a surgical microscope 4 (also referred to below as internal pose detection device) or by a microscope-external optical pose detection device 5 (referred to below as external pose detection device). The pose information can be determined in a reference coordinate system (not shown). By way of example, the pose information may include one or more position value(s) and/or one or more orientation value(s) of the instrument 2 in relation to this reference coordinate system. This has already been explained above.

The pose information can be an image representation of the instrument or can be determined by evaluating exactly one image representation or multiple image representations, in particular by an evaluation device 6, 7.

In a second step S2, there is a check as to whether a biunique determination of the pose of the instrument 2 is possible on the basis of the pose information. Such a biunique determination may be possible if the pose is completely determinable, that is to say in particular if it is possible to determine all three position values and all three orientation values of an instrument-specific coordinate system relative to the reference coordinate system and if this determination is biunique, that is to say the pose information determined in the first step S1 can only be determined in a single pose, in particular not in a plurality of poses, of the instrument 2. If such a biunique determination of the pose of the instrument 2 is possible, the method can end and optionally be carried out at a later time.

If the biunique determination has been identified as impossible in the second step S2, additional information for determining the pose of the instrument 2 more accurately is evaluated in a third step S3. This additional information may be determined by a suitable determination device in a determining step SB. In this case, the determining step SB can be carried out before the third step S3, especially if no biunique determination was detected in the second step S2. By way of example, it is possible that the determining step SB is carried out before the first step S1, simultaneously with the first step S1, between the first step S1 and the second step S2, simultaneously with the second step S2, or else between the second step S2 and the third step S3.

In particular, the additional information can likewise be an image representation. It is also possible for the additional information to be pose information, with this pose information likewise being determined by evaluating exactly one or else multiple image representation/representations.

The pose of the instrument 2 is determined more accurately by way of the evaluation in the third step S3. In particular, it is possible, following the third step S3, that is to say on the basis of the pose information determined in the first step S1 and the additional information determined in the determining step SB, for at least one additional position value and/or at least one additional orientation value to be facilitated vis-à-vis what is possible on the basis of only the pose information determined in the first step. It may also be possible that a biunique determination of the pose of the instrument 2 is possible following the third step S3, especially if a complete but not biunique pose determination is possible on the basis of only the pose information determined in the first step S1.

It is possible that the pose information is determined by the aforementioned internal pose detection device of the surgical microscope 4 in the first step S1 and the additional information is produced or determined by evaluating at least one image representation or is formed by the image representation, which was produced by an image capturing device 8 of the surgical microscope 4 that is not a constituent part of this internal pose detection device. This image capturing device 8, which is not a constituent part of the internal pose detection device, can be in particular an image capturing device, of the surgical microscope 4, for microscopic imaging. It is also possible for the additional information to be produced or determined by evaluating at least one image representation or to be formed by the image representation, which was/were produced by an image capturing device 9a, 9b of the external pose detection device 5. Further, for producing the image representation by the image capturing device 8 of the surgical microscope 4, it is possible that a captured region of this image capturing device 8 is maximized, that is to say in particular for carrying out the determining step SB.

It is also possible that the pose information is determined by the external pose detection device 5 in the first step S1, with the additional information being produced or determined by evaluating at least one image representation or being formed by the image representation which was produced in an image capturing device 8, 10 of the surgical microscope 4, in particular by an image capturing device 8 for microscopic imaging or by what is known as a surround camera 10, with the latter being an image capturing device of the internal pose detection device of the microscope 4.

It is further possible that the additional information determined in the determining step is spatial and/or temporal context information. This has already been explained above. By way of example, spatial context information can be information about a relative pose between an operating table or a patient and the instrument. By way of example, temporal context information can relate to how the instrument has moved previously and/or from where/with what orientation said instrument was introduced into a captured region of an image capturing device. Context information can be acquired by way of a fixed set of rules or can be determined by way of machine learning methods.

Figure 2:
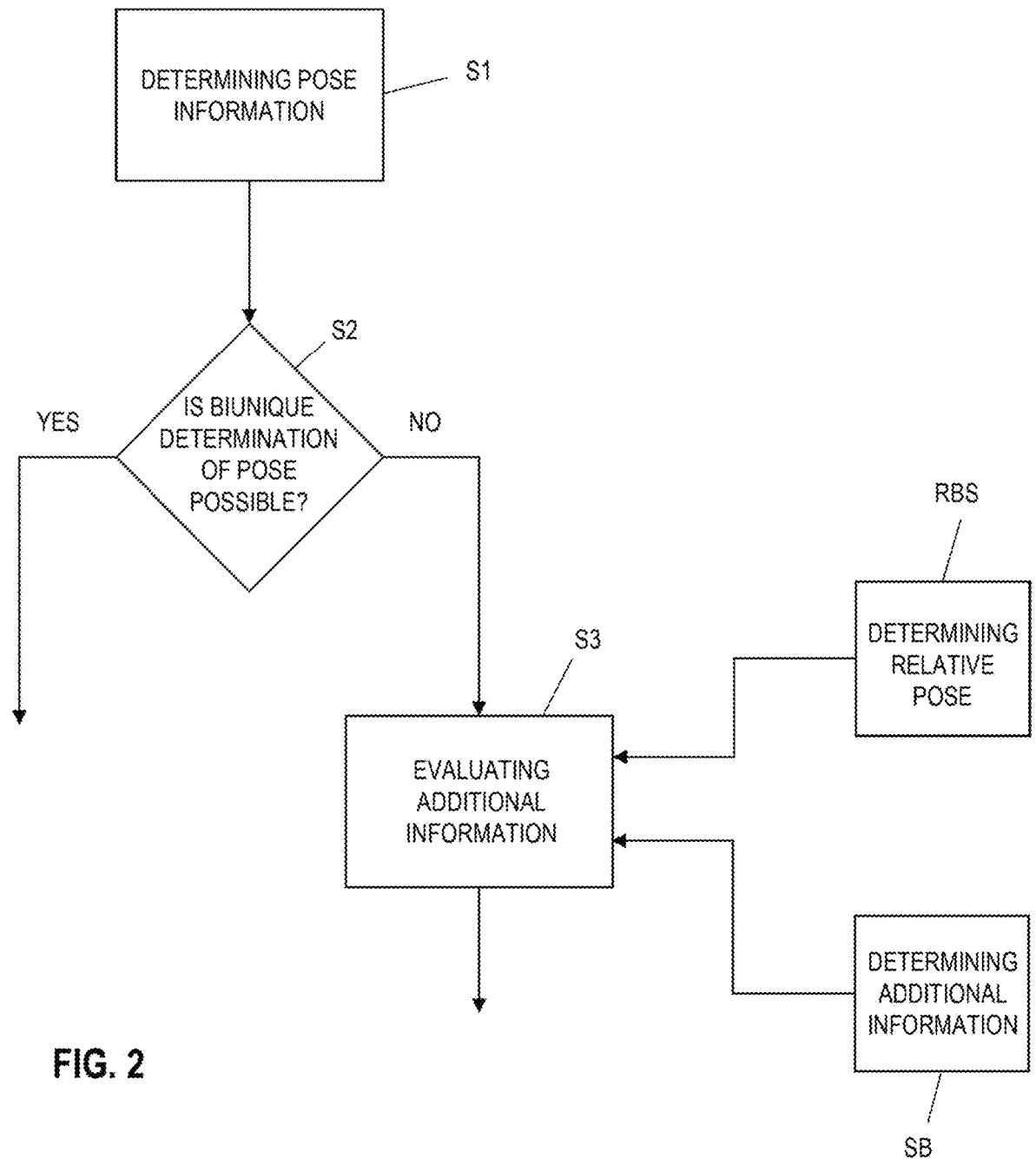
FIG. 2 shows a schematic flowchart of a method according to a further exemplary embodiment of the disclosure.

FIG. 2 shows a schematic flowchart of a method according to a further exemplary embodiment of the disclosure. In contrast to the exemplary embodiment of the method depicted in FIG. 1, the exemplary embodiment depicted in FIG. 2 includes a relative pose determining step RBS, which can be carried out before the determining step B S, simultaneously with the determining step BS, or else after the determining step BS. Then, in the third step S3, the more accurate pose can be additionally determined on the basis of the information about this relative pose.

By way of example, it is possible that the pose information is determined by the external pose detection device 5 in the first step S1 and an image representation for determining the additional information is produced by the image capturing device for microscopic imaging or by the surround camera 10, with the external pose detection device 5 completely or incompletely determining a pose of the surgical microscope 4, for example assisted by markers arranged on the surgical microscope 4.

Naturally, a reversed setup is also conceivable, with the pose information being determined by the pose detection device of the surgical microscope 4 in the first step S1 and an image representation for determining the additional information being produced by the image capturing device of the external pose detection device 5, with the internal pose detection device completely or incompletely determining a pose of the external pose detection device 5, for example assisted by markers arranged on the external pose detection device.

In this case, the information about the relative pose may be known in advance or determined at run-time. This has already been explained above.

Figure 3:
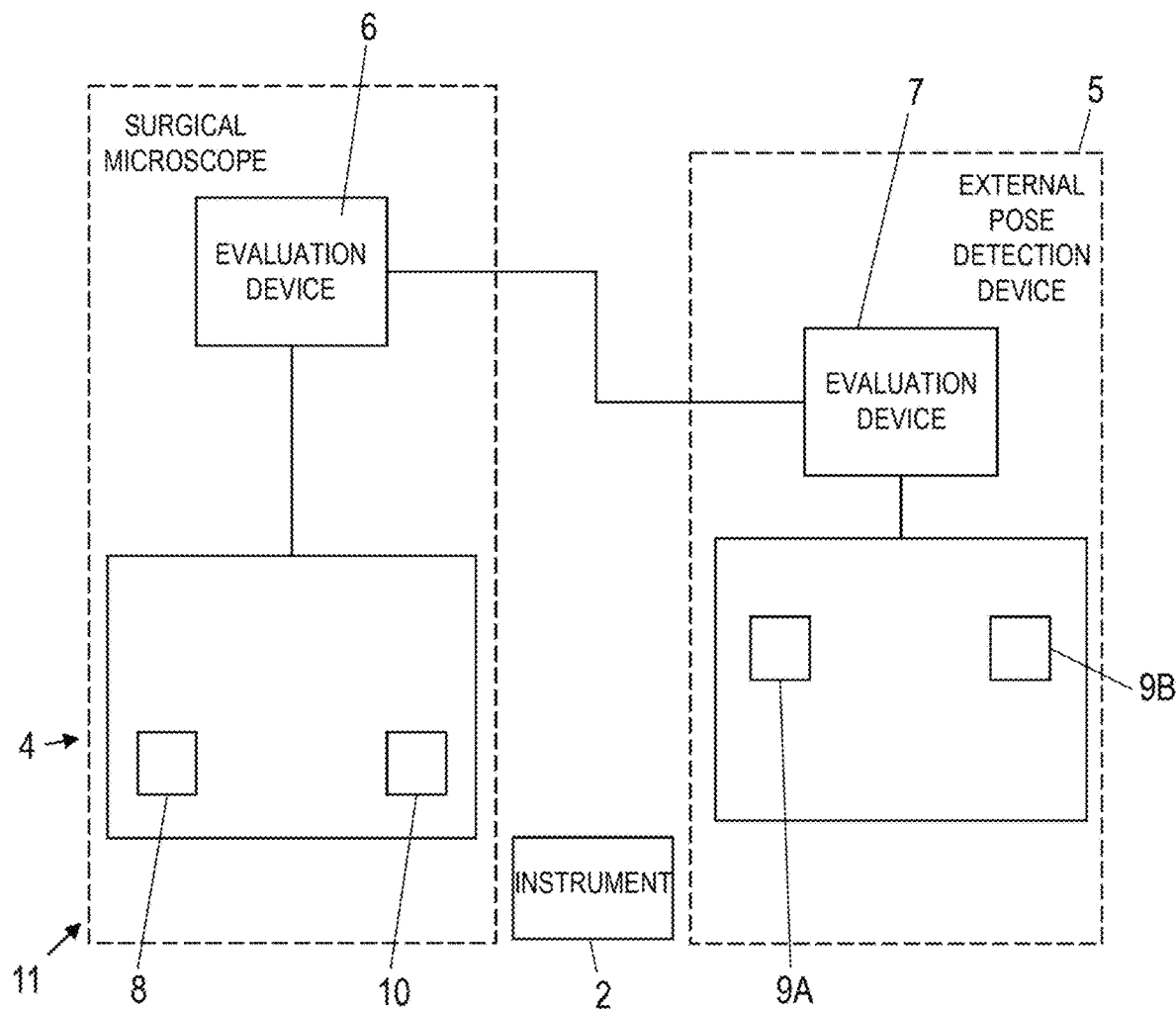
FIG. 3 shows a schematic block diagram of a system according to an exemplary embodiment of the disclosure.

FIG. 3 shows a schematic block diagram of a system 11 according to an exemplary embodiment of the disclosure for optically capturing the pose of at least one instrument 2 in an operating theater.

The system 11 includes an optical pose detection device of a surgical microscope 4, with this pose detection device including a surround camera 10, in particular exactly one surround camera 10, and an evaluation device 6. In this case, the evaluation device 6 can be part of a control and/or evaluation device of the microscope 4. Alternatively, but typically cumulatively, the system includes a microscope-external pose detection device 5, with the latter being configured as a stereo camera system in the depicted exemplary embodiment and including two image capturing devices 9a, 9b.

Further, this external pose detection device 5 includes an evaluation device 7 for determining pose information on the basis of the image representations produced by the image capturing devices 9a, 9b. However, it is also possible that the external pose detection device 5 is a monoscopic pose detection device.

In this case, the system 11 depicted in FIG. 3 is configured to carry out a method according to one of the exemplary embodiments described in this disclosure, in particular according to the exemplary embodiments depicted in FIG. 1 or FIG. 2, of the method for optically detecting the pose.

Markers are not depicted in FIG. 3, with one or more markers being able to be arranged in each case on the instrument 2, on the microscope 4 and/or on a constituent part of the external pose detection device 5. In this case, the external pose detection device 5 may be configured in particular to detect infrared markers, that is to say markers that emit or reflect infrared light, with the internal pose detection device being configured in particular to capture optical markers, in particular an ARUCO marker.

It is possible that the evaluation device 6 of the surgical microscope 4 or the evaluation device 7 of the external pose detection device 5 or else a further evaluation device (not shown) carries out the method, in particular the second step S2 and the third step S3.

It is further possible that the surgical microscope 4 and the external pose detection device 5 are arranged relative to one another in such a way that captured regions of the pose detection devices 5 or of the image capturing device 8 for microscopic imaging overlap at least in part, that is to say the instrument 2 can be imaged by different image capturing devices.

Figure 4:
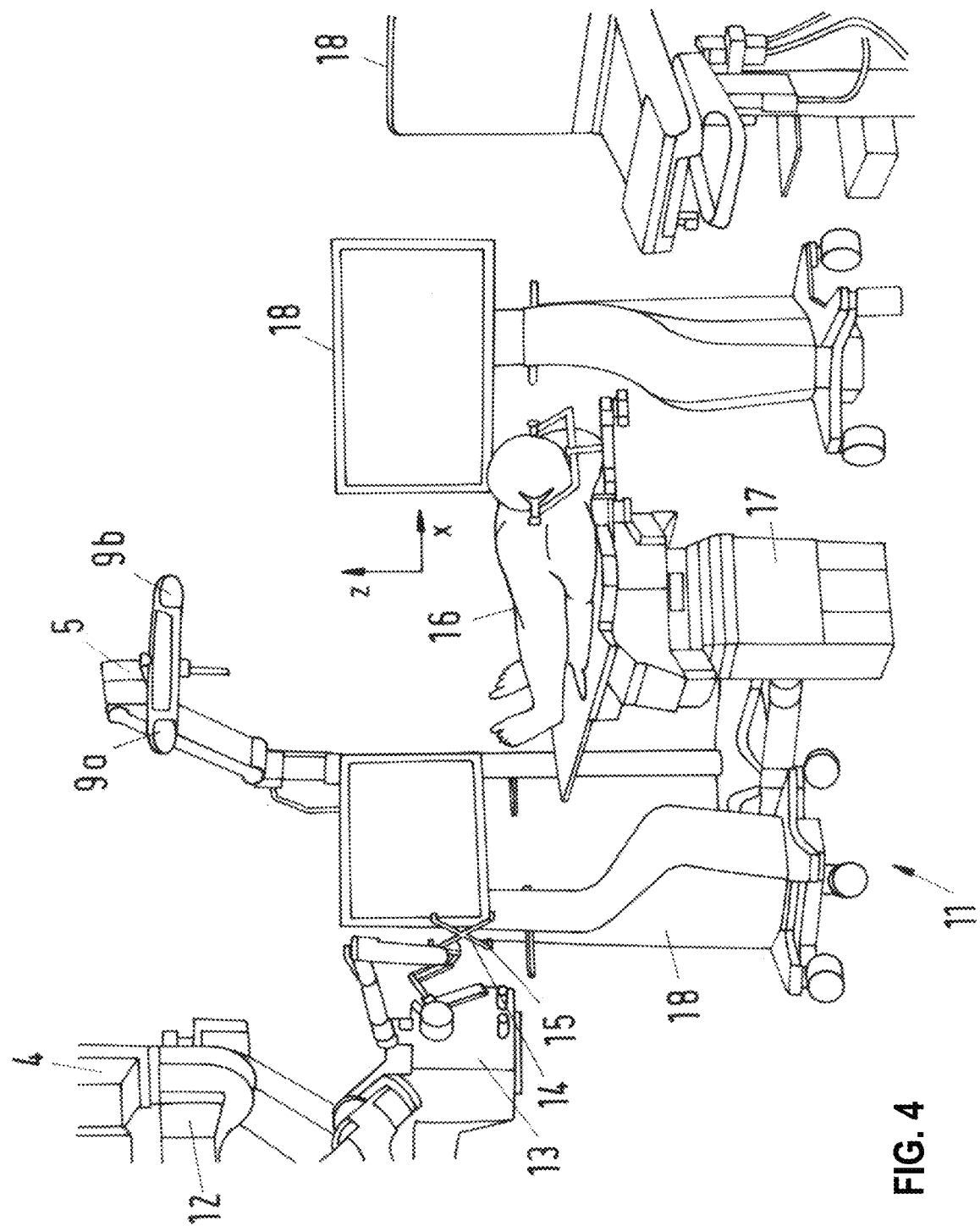
FIG. 4 shows a schematic representation of an operating theater with a system according to an exemplary embodiment of the disclosure.

FIG. 4 shows a schematic representation of an operating theater with a system 11 according to an exemplary embodiment of the disclosure. A surgical microscope 4 is depicted, the latter including a stand 12 for mounting an objective 13 which is arranged at a free end of the stand 12. The stand 12 permits a movement of the objective 13 for changing the pose, that is to say the position and/or orientation of the surgical microscope 4. A reference coordinate system is depicted with a vertical axis z and a longitudinal axis x. The vertical axis z is here parallel to the direction of a gravitational force and is oriented counter to the latter. The longitudinal axis x is perpendicular to the vertical axis z. A transverse axis (not shown) of the reference coordinate system is here perpendicular to the longitudinal and vertical axes x, z, wherein the axes x, z form a Cartesian coordinate system. The stand 12 shown is an example of a kinematic structure for mounting and moving the surgical microscope 4. A person skilled in the art will of course know that other kinematic structures may also be used. The stand 12 includes drive devices (not shown) for moving the objective 13.

Both a surround camera 10 and an image capturing device 8 for microscopic imaging (see FIG. 3) are arranged in the housing of the objective 13, with the beam paths for beam guidance to these image capturing devices 8, 10 being formed separately from one another. The surround camera 10 is part of an internal pose detection device for detecting a pose of an instrument 2 (not shown in FIG. 4), which can be held and moved by a user, for example a surgeon. A target 14 with three markers 15 is depicted, with only one marker 15 being provided with a reference sign for the sake of clarity. The target 14 is arranged to be stationary relative to the objective 13, in particular fastened to the latter. The markers 15 can be IR radiation-reflecting markers 15 and are detected by an external pose detection device 5, which is in the form of a stereo camera system in FIG. 4. It is possible that one or more markers 15 is/are likewise fastened to an instrument 2.

The pose of an object can be at least partly determined using the internal and/or external pose detection device 5 by virtue of the pose of a marker 15 or target 14 being determined, in particular in image-based fashion, with the pose of the object then also being able to be determined on account of the stationary arrangement of the target 14/marker 15 relative to the object. A patient 16 lying on an operating table 17 and a plurality of display devices 18 are also depicted.

It is understood that the foregoing description is that of the exemplary embodiments of the disclosure and that various changes and modifications may be made thereto without departing from the spirit and scope of the disclosure as defined in the appended claims.

What is claimed is:

1. A method for optically detecting a pose of at least one instrument in an operating theater, the method comprising:
   determining pose information of the at least one instrument with an optical pose detection device of a surgical microscope or with a microscope-external optical pose detection device;
   determining with an evaluation device whether the pose information is biunique or whether a biunique determination of the pose of the at least one instrument is possible; and
   detecting with the evaluation device the pose of the at least one instrument by combining the pose information and additional information to determine more accurate pose information when no biunique determination of the pose of the at least one instrument is possible,
   wherein the pose information of the at least one instrument is determined by the microscope-external optical pose detection device and the additional information is produced by evaluating at least one image representation produced by an image capturing device of the surgical microscope.

2. The method as claimed in claim 1, further wherein the more accurate pose information is additionally determined based on information about a relative pose between a coordinate system of the optical pose detection device and an image coordinate system of the image representation evaluated for the purposes of determining the additional information.

3. The method as claimed in claim 2, wherein the information about the relative pose is determined at the run-time or is known in advance.

4. The method as claimed in claim 3, wherein the information about the relative pose is determined by virtue of the pose of the image capturing device for producing the image representation evaluated for the purposes of determining the additional information being determined by the optical pose detection device or by virtue of a pose of the optical pose detection device being determined by evaluating the image representation which is evaluated for the purposes of determining the additional information and which was produced by an image capturing device, and/or by virtue of applying a heuristic.

5. The method as claimed in claim 1, further comprising: determining at least one item of temporal and/or spatial context information, the additional information being determined by evaluating this context information or the additional information being temporal and/or spatial context information.

6. The method as claimed in claim 5, wherein spatial context information is information:
about the relative pose between the at least one instrument and at least one further object in the operating theater, about a target pose of the at least one instrument, in particular a target relative pose in relation to a further object in the operating theater, and
about a relative pose between a plurality of instrument markers.

7. The method as claimed in claim 5, wherein temporal context information is information:
about a movement of the at least one instrument or at least one instrument marker,
about a relative movement between the at least one instrument and a further object in the operating theater, and
about a relative movement between various instrument markers.

8. The method as claimed in claim 5, further comprising: additionally determining at least one item of spatial and/or temporal context information based on information about an instrument geometry or instrument configuration, this being known in advance or determined at run-time.

9. The method as claimed in claim 1, wherein the determination of the additional information is a model-based determination and/or an evaluation of additional information for the purposes of determining more accurate pose information is a model-based evaluation, a model having been produced by machine learning.

10. The method as claimed in claim 9, wherein the determination of the additional information and/or the evaluation of the additional information is carried out user-specifically or surgery-type-specifically.

11. A method for optically detecting a pose of at least one instrument in an operating theater, the method comprising:
determining pose information of the at least one instrument with an optical pose detection device of a surgical microscope or with a microscope-external optical pose detection device;
determining with an evaluation device whether the pose information is biunique or whether a biunique determination of the pose of the at least one instrument is possible; and
detecting with the evaluation device the pose of the at least one instrument by combining the pose information and additional information to determine more accurate pose information when no biunique determination of the pose of the at least one instrument is possible, and
wherein the pose information of the at least one instrument is determined by the optical pose detection device of the surgical microscope and the additional information is produced by evaluating at least one image representation produced by an image capturing device of the surgical microscope which is not a constituent part of the pose detection device, or by an image capturing device of a microscope system-external pose detection device.

12. The method as claimed in claim 11, further comprising:
increasing a captured region of the image capturing device, in particular maximized, for producing the image representation by the image capturing device of the surgical microscope.

13. A system for optically detecting a pose of at least one instrument in an operating theater, the system comprising:
an optical pose detection device of a surgical microscope or a microscope-external pose detection device; and
an evaluation device configured to:
determine pose information of the at least one instrument with the optical pose detection device of the surgical microscope or with a microscope-external optical pose detection device,
determine whether the pose information is biunique or whether a biunique determination of the pose of the at least one instrument is possible, and
detect the pose of the at least one instrument by combining the pose information and additional information to determine more accurate pose information when no biunique determination of the pose of the at least one instrument is possible,
wherein the pose information of the at least one instrument is determined by the microscope-external optical pose detection device and the additional information is produced by evaluating at least one image representation produced by an image capturing device of the surgical microscope.

14. The system as claimed in claim 13, further comprising:
at least one image capturing device of the surgical microscope, which is a constituent part of the optical pose detection device of the surgical microscope, and/or
at least one image capturing device of the surgical microscope, which is not a constituent part of the optical pose detection device of the surgical microscope.

15. A system for optically detecting a pose of at least one instrument in an operating theater, the system comprising:
an optical pose detection device of a surgical microscope or a microscope-external pose detection device; and
an evaluation device configured to:
determine pose information of the at least one instrument with the optical pose detection device of the surgical microscope or with a microscope-external optical pose detection device,
determine whether the pose information is biunique or whether a biunique determination of the pose of the at least one instrument is possible, and
detect the pose of the at least one instrument by combining the pose information and additional information to determine more accurate pose information when no biunique determination of the pose of the at least one instrument is possible,
wherein the pose information of the at least one instrument is determined by the optical pose detection device of the surgical microscope and the additional information is produced by evaluating at least one image representation produced by an image capturing device of the surgical microscope which is not a constituent part of the pose detection device, or by an image capturing device of a microscope system-external pose detection device.

* * * * *

UNITED STATES PATENT AND TRADEMARK OFFICE
CERTIFICATE OF CORRECTION

PATENT NO. : 12,367,604 B2
APPLICATION NO. : 17/856957
DATED : July 22, 2025
INVENTOR(S) : Dominik Litsch and Stefan Saur It is certified that error appears in the above-identified patent and that said Letters Patent is hereby corrected as shown below:

On the Title Page

Item (56) U.S. PATENT DOCUMENTS:

Replace "9,392,931 B2 7/2016 Urban" with "9,392,931 B2 7/2016 Urban et al."

Replace "9,494,518 B2 11/2016 Yang" with "9,494,518 B2 11/2016 Yang et al."

Replace "10,045,831 B2 8/2018 El-Haddad" with "10,045,831 B2 8/2018 El-Haddad et al."

Replace "10,191,268 B2 1/2019 Leger" with "10,191,268 B2 1/2019 Leger et al."

Replace "10,786,323 B2 9/2020 Ang" with "10,786,323 B2 9/2020 Ang et al."

Replace "11,062,465 B2 7/2021 Stopp" with "11,062,465 B2 7/2021 Stopp et al."

Replace "2003/0031349 A1 2/2003 Giorgi" with "2003/0031349 A1 2/2003 Giorgi et al."

Replace "2012/0320186 A1 12/2012 Urban" with "2012/0320186 A1 12/2012 Urban et al."

Replace "2013/0184571 A1 7/2013 Wilkening" with "2013/0184571 A1 7/2013 Wilkening et al."

Replace "2016/0324593 A1 11/2016 El-Haddad" with "2016/0324593 A1 11/2016 El-Haddad et al."

Replace "2020-0100847 A1 4/2020 Siegler" with "2020-0100847 A1 4/2020 Siegler et al."

Replace "2020/0193622 A1 6/2020 Stopp" with "2020/0193622 A1 6/2020 Stopp et al."

Replace "2021/0186627 A1 6/2021 Winne" with "2021/0186627 A1 6/2021 Winne et al."

Signed and Sealed this
Twenty-third Day of September, 2025

John A. Squires
*Director of the United States Patent and Trademark Office*

Replace "2032/0390021 A1 12/2023 Polchin" with "2032/0390021 A1 12/2023 Polchin et al."

Replace "2024/0299100 A1 9/2024 Minne" with "2024/0299100 A1 9/2024 Minne et al."